United States Patent [19]

Cianci et al.

[11] Patent Number: 4,595,102
[45] Date of Patent: Jun. 17, 1986

[54] KIT FOR PERFORMING A MEDICAL PROCEDURE

[75] Inventors: James P. Cianci, Cary; James L. Jessup, Elk Grove Village; Daniel J. Seeley, Barrington, all of Ill.

[73] Assignee: The Kendall Company, Boston, Mass.

[21] Appl. No.: 800,496

[22] Filed: Nov. 21, 1985

Related U.S. Application Data

[63] Continuation of Ser. No. 683,057, Dec. 18, 1984, abandoned.

[51] Int. Cl.⁴ ............................................. B65D 85/62
[52] U.S. Cl. .............................. 206/572; 206/45.31; 206/370; 206/558; 220/23; 220/23.2
[58] Field of Search ................... 206/363-370, 206/45.31, 518, 557, 558, 562, 563, 564, 568-572, 223, 565, 561, 361, 362, 372, 373; 220/23, 23.83, 23.86, 377, 410, 468, 23.2, 23A, 212, 82 R; D7/37, 38

[56] References Cited

U.S. PATENT DOCUMENTS

| | | | |
|---|---|---|---|
| 3,524,564 | 8/1970 | Schuman | 220/82 R |
| 3,780,468 | 12/1973 | MaNett | 220/324 X |
| 3,802,555 | 4/1974 | Grasty et al. | 206/223 |
| 3,851,649 | 12/1974 | Villeri | 206/564 X |
| 3,877,603 | 4/1975 | Holz | 220/23.83 |
| 4,153,160 | 5/1979 | Leigh | 206/370 |
| 4,202,465 | 5/1980 | McLaren | 220/468 |
| 4,226,328 | 10/1980 | Beddow | 206/364 |
| 4,293,074 | 10/1981 | Dunsky | 206/572 |
| 4,353,694 | 10/1982 | Pelerin | 206/369 X |
| 4,501,363 | 2/1985 | Isbey, Jr. | 206/570 |

FOREIGN PATENT DOCUMENTS

| | | | |
|---|---|---|---|
| 1234794 | 10/1960 | France | 220/23.8 |
| 2297023 | 8/1976 | France | 220/23.83 |

*Primary Examiner*—William Price
*Assistant Examiner*—Bryon Gehman
*Attorney, Agent, or Firm*—Powell L. Sprunger

[57] ABSTRACT

A kit for performing a medical procedure comprising, a procedure tray having a plurality of recesses to receive procedural components. The kit has a prepping tray having a plurality of recesses to receive prepping components, with the prepping tray being disposed in a side-by-side relationship with the procedure tray. The prepping tray has an outwardly directed upper transparent flange which is sufficiently large to cover the procedure tray.

1 Claim, 3 Drawing Figures

U.S. Patent   Jun. 17, 1986   4,595,102
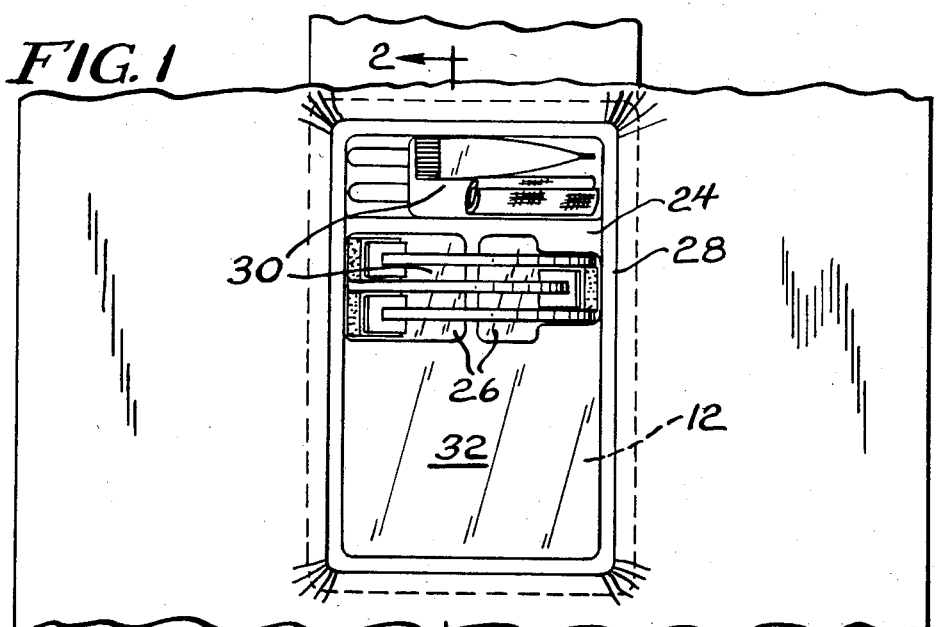
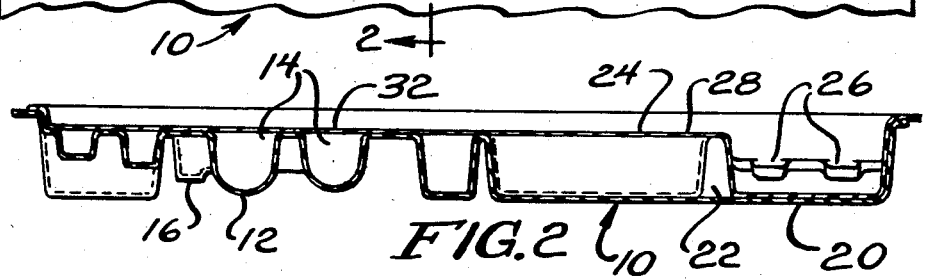
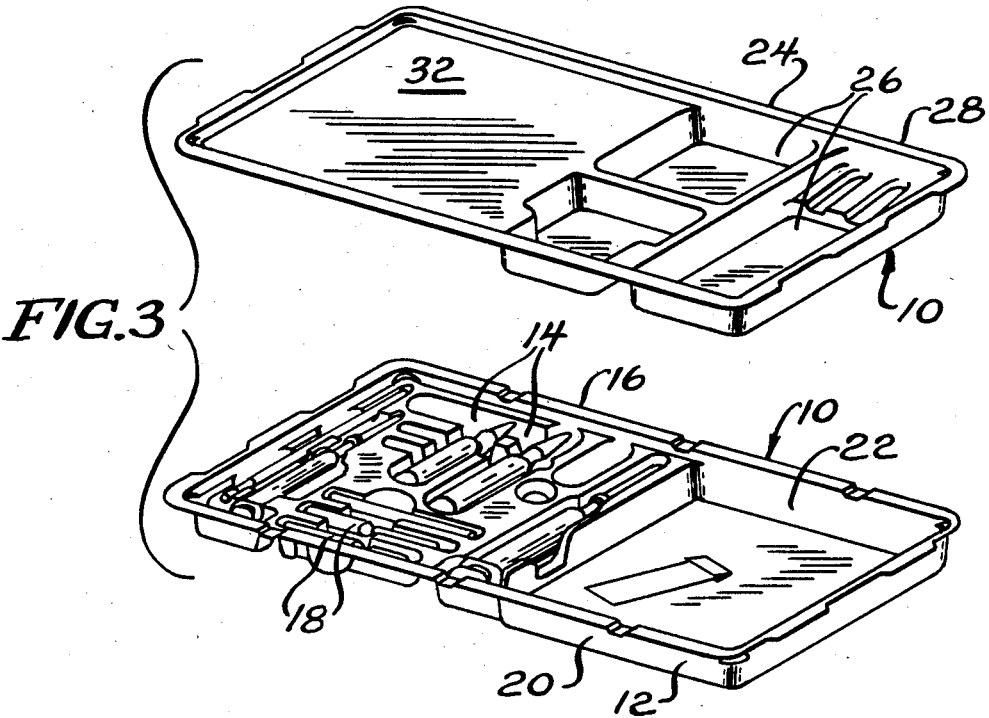

KIT FOR PERFORMING A MEDICAL PROCEDURE

This is a continuation of application Ser. No. 683,057 filed Dec. 18, 1984, now abandoned.

BACKGROUND OF THE INVENTION

The present invention relates to kits for performing a medical procedure.

Many medical procedures, particularly regional anesthesia procedures, require skin preparation with an antiseptic solution prior to initiation of the insertion of various needles or catheters into the patient. The components of kits for such procedures can be segregated into those for the prepping part of the procedure and those for the invasive part of the procedure. Examples of such kits are spinal anesthesia trays or percutaneous cardiovascular catheter insertion trays.

It is desirable to isolate the prepping components of such kits from the procedural components in order that the procedural components are not inadvertently contaminated during prepping of the patient. In the past, double-deck trays have been used with the prepping tray being seated over the procedural tray. However, this configuration has proved inconvenient since the prepping tray must be removed to inspect the procedural tray to verify that all procedural components are present and ready for use.

SUMMARY OF THE INVENTION

A principal feature of the present invention is the provision of an improved kit for performing a medical procedure.

The kit of the invention comprises a procedure tray having a plurality of recesses to receive procedural components. The kit has a prepping tray having a plurality of recesses to receive prepping components, with the prepping tray being disposed in a side-by-side relationship with the procedure tray. The prepping tray has an outwardly directed upper transparent flange which is sufficiently large to cover the procedure tray.

A feature of the present invention is that the procedural components may be inspected through the flange without removal of the prepping tray.

Another feature of the invention is that the flange protects the procedural components from contamination during prepping of the patient.

Yet another feature of the invention is that the kit has a low profile.

A feature of the invention is that the flange may be used as a working space during prepping.

A further feature of the invention is that the prepping tray may be discarded after prepping the patient in order to expose the procedural components.

Another feature of the invention is that the procedure tray has an outwardly directed extension defining a cavity to receive the component portion of the prepping tray.

A feature of the invention is that the cavity may be used to discard components during the procedure.

Further features will become more fully apparent in the following description of the embodiments of this invention and from the appended claims.

DESCRIPTION OF THE DRAWINGS

In the drawings:

FIG. 1 is an upper plan view of a kit of the present invention;

FIG. 2 is a sectional view taken substantially as indicated along the line 2—2 of FIG. 1; and FIG. 3 is an exploded perspective view of the kit of FIG. 1.

DESCRIPTION OF THE PREFERRED EMBODIMENTS

Referring now to FIGS. 1-3, there is shown a kit generally designated 10 for performing a medical procedure such as a spinal anesthesia procedure or a percutaneous cardiovascular catheter insertion procedure.

The kit 10 has a lower procedure tray 12 having a plurality of recesses 14 in a component portion 16 of the tray 12 to receive procedural components 18. The tray 12 has an outwardly directed extension 20 defining a cavity 22 for a purpose which will be described below. The tray 12 and components 18 are sterile, and the tray 12 may be made of any suitable plastic material.

The kit 10 has an upper prepping tray 24 having a plurality of recesses 26 in a component portion 28 of the tray 24 to receive prepping components 30. As shown, the tray 24 has an outwardly directed upper transparent flange 32 extending from the component portion 28. The component portion 28 of tray 24 is received in the cavity 22 of extension 20, such that the trays 12 and 24 are disposed in a side-by-side relationship. Also, in this configuration, the flange 32 is sufficiently large to cover the component portion 16 of tray 12 and the components 18. The tray 24 and components 30 are in a sterile condition, and the tray 24 may be made of any suitable plastic material.

In use, the kit 10 is opened in order to expose the components 30 in prepping tray 24. The prepping components 30 are utilized to prep the patient while the flange 32 protects the procedural components 18 from contamination. Also, the flange 32 may be used as a working space during prepping of the patient. Further, the procedural components 18 may be visualized through the transparent flange 32 prior to prepping in order to verify that all of the components 18 are intact and ready for use. After prepping of the patient has been completed, the tray 24 may be removed from the tray 12 and may be discarded, thus exposing the procedural component 18 for use in the procedure. During the procedure, the cavity 22 may be utilized to discard various components 18.

The foregoing detailed description is given for clearness of understanding only and no unnecessary limitations should be understood therefrom as modifications will be obvious to those skilled in the art.

We claim:

1. A kit for performing a medical procedure, comprising:

a lower procedure tray having a component portion defining a plurality of recesses, said component portion extending the width of the procedure tray at one end of the tray, said procedure tray having an outwardly directed extension defining a cavity spaced from the component portion of the procedure tray, said cavity extending the width of the procedure tray at the other end of the tray;

a plurality of procedural components received in the recesses of the procedure tray;

an upper prepping tray having a component portion received in the cavity with a plurality of recesses, said component portion of the prepping tray extending the width of the prepping tray at one end of the prepping tray, said recesses of the prepping tray extending the depth of the procedure tray cavity, said component portion of the prepping tray being disposed in a side-by-side relationship with the component portion of the procedure tray, said prepping tray having an outwardly directed upper generally planar transparent flange extending from the component portion of the prepping tray which is sufficiently large to cover the component portion of the procedure tray, said flange extending the width of the prepping tray at the other end of the prepping tray; and a plurality of prepping components received in the recesses of the prepping tray.

* * * * *